US010639270B2

(12) United States Patent
Feuer et al.

(10) Patent No.: US 10,639,270 B2
(45) Date of Patent: May 5, 2020

(54) FOAMING OIL CLEANSER COMPOSITION

(71) Applicant: L'OREAL, Paris (FR)

(72) Inventors: William Ronald Feuer, Hillsborough, NJ (US); Miao Wang, Westfield, NJ (US); Wivina Lijo, Flemington, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/906,457

(22) Filed: Feb. 27, 2018

(65) Prior Publication Data
US 2019/0262258 A1 Aug. 29, 2019

(51) Int. Cl.
| *A61K 8/92* | (2006.01) |
| *A61K 8/46* | (2006.01) |
| *A61Q 19/10* | (2006.01) |
| *A61K 8/49* | (2006.01) |
| *A61K 8/04* | (2006.01) |
| *A61K 8/34* | (2006.01) |

(52) U.S. Cl.
CPC .............. *A61K 8/922* (2013.01); *A61K 8/046* (2013.01); *A61K 8/345* (2013.01); *A61K 8/466* (2013.01); *A61K 8/498* (2013.01); *A61Q 19/10* (2013.01)

(58) Field of Classification Search
CPC ...................................................... A61K 8/922
USPC ......................................................... 514/458
See application file for complete search history.

(56) References Cited

U.S. PATENT DOCUMENTS

| 4,130,548 A | 12/1978 | Kochanowski |
| 6,132,738 A | 10/2000 | Lerg et al. |
| 6,306,410 B1 | 10/2001 | Doki |
| 6,620,773 B1 | 9/2003 | Stork et al. |
| 9,320,697 B2 | 4/2016 | Kleinen et al. |

*Primary Examiner* — Kevin E Weddington
(74) *Attorney, Agent, or Firm* — Laetitia Leproust; Runzhi Zhao

(57) ABSTRACT

A foaming oil cleanser composition and a method of preparing a foaming oil cleanser composition are provided. The foaming oil cleanser composition includes (a) a dialkyl sulfosuccinate, (b) *Ricinus Communis* Seed Oil, and (c) one or more oils. The foaming oil cleanser composition is essentially free of water and sulfate.

21 Claims, No Drawings

FOAMING OIL CLEANSER COMPOSITION

FIELD OF THE DISCLOSURE

The present disclosure relates to a cleansing oil composition. More particularly, the disclosure relates to a foaming oil cleanser composition.

BACKGROUND

Surfactants are widely used in aqueous based personal care, household, and industrial products. They are typically used as wetting agents, detergents, and emulsifiers. In personal care cleansing products (e.g., shampoos, body washes, facial cleansers, liquid hand soaps, etc.) the surfactant is often the most important component because it provides many of the cleansing attributes of the composition.

Although in principle any surfactant class (e.g., cationic, anionic, nonionic, amphoteric) is suitable in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are often used as detersive agents in cleansers and cleaning products because of their excellent cleaning and foaming properties. From the consumer's perspective, the amount and stability of the foam directly relates to the perceived cleaning efficiency of the composition. Generally speaking, the larger the volume of foam produced and the more stable the foam, the more efficient is the perceived cleaning action of the composition. This presents a potential problem for anhydrous, oil based cleansers, as foam volume tends to decrease in the presence of oils due to their defoaming impacts on surfactants. And while oil based cleansers have the advantage of providing an emolliency to the skin and off-setting the potential drying effects of the cleansing surfactants, the perception of the formula is that it is not efficacious due to their low foaming characteristics.

Sulfate-based surfactants (such as, for example, sodium lauryl sulfate and sodium lauryl ether sulfate) are particularly popular because of their effectiveness in cleansing, foam production, and stability. Personal care cleansers containing sulfate-based surfactants are also generally easy to thicken with typical thickeners, such as salt and cellulose-based materials. Nonetheless, these particular surfactants can be more drying than some sulfate free alternatives. For instance, over-use of sulfate-based surfactants can cause needless drying to the face and scalp, and contribute to color fading and drying of hair. Eliminating sulfate surfactants from cleansing compositions has been challenging because sulfate-free compositions typically have poor foaming properties, are difficult to thicken, are not clear (not transparent). Also, the cleansing ability of sulfate-free composition are often sub-optimal.

In view of the remarks above, there is a need to provide a readily high foaming, oil based, anhydrous cleanser formulation.

SUMMARY OF THE DISCLOSURE

The instant disclosure relates to foaming oil cleansers comprising:
(a) from about 1% to about 25% of dialkyl sulfosuccinate;
(b) from about 2% to about 60% of *Ricinus Communis* Seed Oil;
(c) from about 35% to about 80% of one or more oils wherein essentially free of water; and
wherein all amounts are percentages by weight based on the total weight of the composition.

In one or more embodiments, the amount of water is less than 0.5%. In some embodiments, the amount of water is less than 0.1%. In one or more embodiments, the foaming oil cleanser is free of water.

In some embodiments, the dialkyl sulfosuccinate is diethylhexyl sodium sulfosuccinate. In one embodiment, the diethylhexyl sulfosuccinate is present in an amount from about 5% to about 21% by weight of the total weight of the composition. In one or more embodiments, the diethylhexyl sodium sulfosuccinate is present in an amount from about 8% to about 15% by weight of the total weight of the composition. In some embodiments, the dialkyl sulfosuccinate is soluble in oil.

In one or more embodiments, the *Ricinus Communis* Seed Oil is present in an amount from about 5% to about 50% by weight of the total weight of the composition. In some embodiments, the *Ricinus Communis* Seed Oil is present in an amount from about 10% to about 30% by weight of the total weight of the composition.

In one or more embodiments, the *Ricinus Communis* Seed Oil stabilizes the diethylhexyl sodium sulfosuccinate.

In one or more embodiments, the oil component is selected from olive oil, coconut oil (*Cocos Nucifera* Oil), avocado oil (*Persea Gratissima* oil, apricot oil, sweet almond oil, castor oil, coriander oil, grapeseed oil, rapeseed oil, hazelnut oil, shea butter, palm oil, apricot kernel oil, rice bran oil (*Oryza Sativa* (rice) Bran Oil), corn germ oil (*Zea Mays* Oil, wheatgerm oil, soybean oil, sunflower oil, evening primrose oil, safflower oil, sesame seed oil, passionflower oil, camellia oil, *Vitis Vinifera* (grape) Oil, and mixtures thereof.

In some embodiments, the composition may further comprise a fatty acid mono or dialkanolamide. In one or more embodiments, the fatty acid dialkanolamide is present in amount of about 0.1% to about 10% by weight of the total weight of the composition. In one embodiment, the fatty acid dialkanolamide is cocamide mono-isopropanolamide.

In some embodiments, the composition may further comprise propylene glycol.

In one or more embodiments, the foaming oil cleanser is sulfate free.

Another aspect of the instant disclosure can include an anhydrous foaming oil cleanser comprising:
(a) from about 8% to about 15% of Diethylhexyl Sodium Sulfosuccinate;
(b) from about 15% to about 30% of *Ricinus Communis* Seed Oil; and
(c) from about 35% to about 80% of oils selected from the group consisting of olive oil, coconut oil (*Cocos Nucifera* Oil), avocado oil (*Persea Gratissima* oil), apricot oil, sweet almond oil, castor oil, coriander oil, grapeseed oil, rapeseed oil, hazelnut oil, shea butter, palm oil, apricot kernel oil, rice bran oil (*Oryza Sativa* (rice) Bran Oil), corn germ oil (*Zea Mays* Oil, wheatgerm oil, soybean oil, sunflower oil, evening primrose oil, safflower oil, sesame seed oil, passionflower oil, camellia oil, *Vitis Vinifera* (grape) Oil, and mixtures thereof.
(d) optional components selected from the group consisting of actives, fragrance, preservatives, and a combination thereof; and
wherein all amounts are percentages by weight based on the total weight of the composition; and wherein the anhydrous foaming oil cleanser is sulfate-free.

In some embodiments, the actives are selected from the group consisting of butylated hydroxytoluene, tocopherol, tocopherol derivatives, tocotrienol, tocotrienol derivatives, ascorbic acid derivatives, ascorbyl palmitate, vitamin E, vitamin C, Vitamin A Palmitate and combinations thereof. In one or more embodiments, the composition may further comprise an additive selected from additional surfactants, fragrances, salts, acids, pH adjusters, and mixtures thereof.

Another aspect of the instant disclosure can include a method of cleansing skin, comprising applying to skin the composition of claim 1.

The foaming oil cleanser compositions of the instant disclosure provide unexpected level of foaming even though they contain a high content of oil and are essentially free of sulfate and water.

It is to be understood that both the foregoing general description and the following detailed description are exemplary and explanatory only, and are not restrictive of the invention.

DETAILED DESCRIPTION OF THE DISCLOSURE

The instant disclosure relates to compositions for cleansing the skin.

The foaming oil cleanser compositions of the instant disclosure, in their broadest sense, typically include the following:
(a) from about 1% to about 25% of dialkyl sulfosuccinate;
(b) from about 2% to about 60% of *Ricinus Communis* Seed Oil; and
(c) from about 35% to about 80% of one or more oils;
wherein the foaming oil cleanser is essentially free of water; and
wherein all amounts are percentages by weight based on the total weight of the composition.

The oil cleanser compositions of the instant disclosure exhibit a surprisingly foaming behavior. The foaming oil cleansers compositions are particularly unique in that they are foaming even though they contain a high content of oil and are essentially free of sulfate and water.

As used herein, the term "essentially sulfate free" means that, while it is preferable that no sulfate is present in the compositions of the invention, it is possible to have very small amounts of sulfate in the compositions, provided that these amounts do not materially affect the advantageous properties of the composition. In particular, "essentially sulfate-free anionic surfactant" means that no traditional sulfate-based anionic surfactants are used in the composition and that the surfactant does not contribute sulfate to the composition. Most preferably, the compositions contain no sulfate. To the extent any sulfate is present in the compositions, it is present at an amount of less than about 2.0% by weight, typically less than about 1.5% by weight, typically less than about 1.0% by weight, typically less than about 0.5% by weight, more typically less than about 0.1% by weight, based on the total weight of the composition. To the extent present, the sulfates in such compositions are typically contributed by components other than the anionic surfactant.

As used herein, the term "foam" means the ability of a composition to produce foam. Both the amount and stability of the foam are measures by the height of the foam when formed.

As used herein, the term "transparent" means that the composition is clear and the oils are properly solubilized. The composition does not haze or opacify.

Dialkyl Sulfosuccinate

In some embodiments, the dialkyl sulfosuccinate of (a), may be, for example, a compound selected from the group consisting of dialkyl sulfosuccinates and/or dialkyl methylsulfosuccinates in which the alkyl radicals have 4 to 24, preferably 6 to 18, particularly preferably 6 to 14, carbon atoms. The alkyl radicals can be linear or branched. Different or identical alkyl radicals can be present in one molecule of dialkyl sulfosuccinate and/or dialkyl methylsulfosuccinates. The dialkyl sulfosuccinate is soluble in oil.

The dialkyl sulfosuccinate may be present in an amount from about 1%, 1.2%, 1.4%, 1.6%, 1.8%, 2%, 2.2%, 2.4%, 2.6%, 2.8%, 3%, 3.5%, 4%, 4.5%, 5%, 5.5%, 6%, 6.5%, 7%, 7.5%, 8%, 8.5% to about 8%, 8.5%, 9%, 9.5%, 10%, 10.5%, 11%, 11.5%, 12%, 13%, 14%, 15%, 16%, 17%, 18%, 20%, 22%, 23%, 24%, or 25%, by weight based on the total weight of the composition. In some embodiments, the dialkyl sulfosuccinate is diethylhexyl sodium sulfosuccinate.

Oils

*Ricinus Communis* Seed Oil (also Known as Castor Oil)

The *Ricinus Communis* Seed Oil may be present in an amount from about 2%, 3%, 4%, 5%, 6%, 7%, 8%, 9%, 10%, 11%, 12%, 12.5%, 13%, 13.5%, 14%, 14.5%, 15% to about 15%, 15.5%, 16%, 16.5%, 17%, 18%, 19%, 20%, 22%, 24%, 26%, 28%, 30%, 32%, 35%, 40%, 45%, 50%, 55% or 60%, by weight based on the total weight of the composition.

In some embodiments, the presence of *Ricinus Communis* Seed Oil helps the stabilization of the diethylhexyl sodium sulfosuccinate.

Other Oils

The foaming oil cleanser of the disclosure include one or more oils that are hydrocarbon-based, preferably selected from plant oils. In some embodiments, the one or more oils of (c), may be, for example, selected from the group consisting of olive oil, coconut oil (*Cocos Nucifera* Oil), avocado oil (*Persea Gratissima* oil), apricot oil, sweet almond oil, castor oil, coriander oil, grapeseed oil, rapeseed oil, hazelnut oil, shea butter, palm oil, apricot kernel oil, rice bran oil (*Oryza Sativa* (rice) Bran Oil), corn germ oil (*Zea Mays* Oil, wheatgerm oil, soybean oil, sunflower oil, evening primrose oil, safflower oil, sesame seed oil, passionflower oil, camellia oil, *Vitis Vinifera* (grape) Oil, and mixtures thereof.

While oils of plant origin are preferred, other hydrocarbon-based oils of mineral or synthetic origin are also useful. Such oils include, for example, volatile or non-volatile liquid paraffins and derivatives thereof, petroleum jelly, mineral oil, perhydrosqualene, polydecenes, isohexadecane, isododecane, and hydrogenated polyisobutene such as Pareamᵀᴹ oil (sold by NOF Corp.), and mixtures thereof.

Other non-silicone fats useful in the invention include, for example, esters and carbonates, as well as triglycerides. Examples of useful esters include C12-15 alkyl benzoate, cetearyl isononanoate, cetyl ethylhexanoate, coco-caprylate/caprate, decyl oleate, ethylhexyl stearate, hexyl laurate, isopropyl myristate, isopropyl palmitate, oleyl erucate, and mixtures thereof.

Examples of carbonates include dicaprylyl ether (available as Cetiol OE from Cognis) and dicaprylyl carbonate (Cetiol CC also from Cognis), Examples of tryglicerides include caprylic/capric triglyceride (sold by Cremer Oleo GmbH & Co. as MIGLYOL® 810 and 812) and caprylic/capric linoleic triglyceride (sold by Cremer Oleo GmbH & Co. as MIGLYOL® 818 and 829), and mixtures thereof.

In some embodiments, the one or more oils of (c) may be present in an amount from about 35%, 36%, 37%, 40%, 45%, 50% to about 50%, 55%, 60%, 65%, 70%, 75% and 80%, by weight based on the total weight of the composition.

Anhydrous Composition

The purpose of the anhydrous medium is to be able to keep the composition transparent. The presence of water would make the composition to haze and to opacify.

As used herein, the term "anhydrous" means that no water is added to the composition and water is contained only in the form of the constitutional water which in some cases cannot be avoided and is brought in as part of the ingredients in very small amounts.

In some embodiments, the foaming oil cleanser composition is essentially free of water. In one or more embodiments, the amount of water may be less than 0.5%. In some embodiments, the amount of water may be less than 0.1%. In one or more embodiments, the foaming oil cleanser is free of water.

Fatty Acid Mono or Dialkanolamide

In addition to the components described above, the foaming oil cleanser composition can additionally include fatty acid mono or dialkanoamides. Non-limiting examples of fatty acid mono or dialkanoamides, in addition to cocamide MIPA, are Cocamide MEA, Cocoamide DIPA.

In some embodiments, the fatty acid mono or dialkanoamide may be present in an amount from about 0.1%, 0.5%, 1%, 2.5%, 3%, 3.5%, 4% to about 4%, 4.5%, 5%, 5.5%, 6%, 7%, 8%, 9% and 10%, by weight based on the total weight of the composition. In some embodiments, the fatty acid dialkanoamide is cocamide MIPA, also known as cocamide mono-isopropanolamide.

Polvols

In addition to the components described above, the foaming oil cleanser compositions can additionally include polyols. Non-limiting examples of polyols, in addition to propylene glycol, are dipropylene glycol, butylene glycol, hexylene glycol, polyethylene glycol, and the mixtures thereof.

The propylene glycol and/or other alkylene glycols may be present in an amount from about 0.1%, 0.2%, 0.5%, 1%, 1.5%, 2%, 2.5% to about 2.5%, 3%, 3.5%, 4%, 5%, 6%, 7% and 10%, by weight based on the total weight of the composition. In some embodiments, the alkylene glycol is propylene glycol.

Surfactants were tested according to the foam criteria. The main property required to select the surfactants was the fact that it needed to be compatible with the anhydrous system.

In selected embodiments, the surfactants are those which can be used in an anhydrous system, such as diethylhexyl sodium sulfosuccinate. In other selected embodiments, the surfactants are those of sulfosuccinates, sulfosuccinamates, and glycinate, and the mixtures thereof.

Optional Components

In one embodiment, the composition may include optional components selected from the group consisting of actives, fragrance, preservatives, and combinations thereof. The actives are selected from the group consisting of butylated hydroxytoluene, tocopherol, tocheropl derivatives, tocotrienol, tocotrienol derivatives, ascorbic acid, ascorbic acid derivatives, ascorbyl palmitate, vitamin E, vitamin C, and combinations thereof.

The compositions may also include any other adjuvant or additive that is usually used in the field of self-cleansing products, in particular shampoos. A person skilled in the art would know which adjuvants and/or additives to select to achieve the desired results (e.g. preservatives) without adversely affecting the properties of claimed emulsions. For example, such additives include preserving agents (e.g. phenoxethanol, sodium benzoate, benzoic acid), consistency regulators (e.g. isopropyl alcohol), thickeners, antioxidants, fragrances, and mixtures thereof.

The above ingredients lists are only examples and not limiting.

The compositions according to the instant disclosure may be prepared according to techniques that are well known to those skilled in the art, in particular those intended for the preparation of shaving compositions.

The instant disclosure will be better understood from the examples that follow, all of which are intended for illustrative purposes only and are not meant to limit the scope of the instant disclosure in any way.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

The expression "one or more" as used herein includes individual components as well as mixtures/combinations.

All ranges and values disclosed herein are inclusive and combinable. For examples, any value or point described herein that falls within a range described herein can serve as a minimum or maximum value to derive a sub-range, etc.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc.

Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

The following examples illustrate the present invention but are not intended to limit the scope of the invention.

TABLE 1

| | | Inventive Examples | |
|---|---|---|---|
| Function | INCI US | Inventive Formula 1 | Inventive Formula 2 |
| Oils | Cocos Nucifera (Coconut) Oil | 6 | 0.5 |
| | Persea Gratissima (Avocado) Oil | 1 | 1 |
| | Vitis Vinifera (Grape) Seed Oil | 1 | 1 |
| | Zea Mays (Corn) Germ Oil | 50.3 | 55.8 |
| | Oryza Sativa (Rice) Bran Oil | 0.5 | 0.5 |
| Oil | Ricinus Communis (Castor) Seed Oil | 20 | 20 |
| Dialkyl Sulfosuccinate | Diethylhexyl Sodium Sulfosuccinate | 12 | 12 |
| Surfactant | Cocamide Mipa | 4 | 4 |
| Solvent | Propylene Glycol | 2.1 | 2.1 |
| Vitamin | Tocopherol | 0.1 | 0.1 |
| Fragrance | Fragrance | 3 | 3 |

The Inventive Examples in Table 1 were prepared according to the procedure as follows: First, Corn Oil was heated to 70-75 C, then Diethylhexyl Sodium Sulfosuccinate was added. The two ingredients were then mixed for 1 hour with a propeller type blade on high speed. Once the mixture started to cool and reached 25 C, Propylene Glycol, Cocamide MIPA Castor Oil were added and mixed until uniform.

Technical Foam Measurements

To evaluate the foam properties and in particular the foam height, tests were performed and the height of the foam was measured. In all the formulas, the total amount of oils as well as surfactants was maintained in order to be able to compare the inventive and comparative formulas. The tests were performed on inventive formulas containing Diethylhexyl Sodium Sulfosuccinate (DSS) with Castor Oil at different concentrations of DSS: 10% (Inventive formula 3), 12% (Inventive formula 1), 15% (Inventive formula 4), and 20% (Inventive formula 5); and on comparative formulas containing TIPA-Laureth Sulfate in oil at three levels of surfactants: 10% (Comparative Formula 1), 15% (Comparative Formula 2), and 20% (Comparative Formula 3). formulas are described in Table 2 below.

The foam heights were respectively between 580 mL and 700 mL for the Experiments containing Diethylhexyl Sodium Sulfosuccinate at the various concentrations and Castor Oil.

The foam heights were respectively between 400 mL and 550 mL for the Experiments containing TIPA-Laureth Sulfate at the various concentrations.

The results demonstrated that formulas containing Diethylhexyl Sodium Sulfosuccinate and Castor Oil (Inventive Formula 3, 4 and 5) exhibited superior foaming compare to the formulas containing TIPA-Laureth Sulfate at the equivalent concentrations (Comparative Formulas 1, 2 and 3). It is also noticed that the foam height increased significantly when the amount of Diethylhexyl Sodium Sulfosuccinate increased. The difference between the foam heights measured are statistically significant and can be perceived by consumers The foam heights achieved with the inventive examples are comparable to classical sodium Laureth Sulfate based shower gels, which are well known by the skill in the arts. This is surprising because in the present disclosure no water is involved. There is no commercially available product on the market in the anhydrous oil cleanser category that shows a level foam comparable to the classical shower gels.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

TABLE 2

| INCI Name | Trade Name | Comparative Formula 1 | Comparative Formula 2 | Comparative Formula 3 | Inventive Formula 3 | Inventive Formula 1 | Inventive Formula 4 | Inventive Formula 5 |
|---|---|---|---|---|---|---|---|---|
| *Zea Mays* (Corn) Germ Oil | Refined Corn Oil | 83 | 78 | 73 | 66 | 64 | 61 | 56 |
| Laureth-3 | Dehydol LS 3 Deo n | 3 | 3 | 3 | | | | |
| TIPA-Laureth Sulfate | Zetesol TP 300 | 10 | 15 | 20 | | | | |
| Propylene Glycol | Propylene Glycol USP/EP | 2 | 2 | 2 | 2 | 2 | 2 | 2 |
| Cocamide MIPA | Rewomid V 3203 | 2 | 2 | 2 | 2 | 2 | 2 | 2 |
| Diethylhexyl Sodium Sulfosuccinate | Aerosol OT 100% Surfactant | | | | 10 | 12 | 15 | 20 |
| *Ricinus Communis* (Castor) Seed Oil | Lipovol Co | | | | 20 | 20 | 20 | 20 |

The tests were performed according to the procedure as follows: A solution of 198 grams of deionized water at 25° C. was mixed with 2.0 grams of experimental formulas in a beaker. The solution was carefully transferred to a 1000 mL volumetric cylinder so as to not create any foaming. A stopper was used to contain the mixture. The volumetric cylinder was inverted 10 times. The height of the foam was measured and recorded.

The results are presented in Table 3 below.

TABLE 3

| | Inventive Formula 3 (10% of DSS) | Comparative Formula 1 (10% of TIPA-Laureth Sulfate) | Inventive Formula 1 (12% of DSS) | Inventive Formula 4 (15% of DSS) | Comparative Formula 2 (15% of TIPA-Laureth Sulfate) | Inventive Formula 5 (20% of DSS) | Comparative Formula 3 (20% of TIPA-Laureth Sulfate) |
|---|---|---|---|---|---|---|---|
| Foam Height (mL) | 580 | 400 | 600 | 610 | 470 | 700 | 550 |

What is claimed is:

1. A foaming oil cleanser composition comprising:
   (a) from about 1% to about 25% of dialkyl sulfosuccinate;
   (b) from about 2% to about 60% of *Ricinus Communis* Seed Oil;
   (c) from about 35% to about 80% of one or more oils
   wherein the foaming oil cleanser composition is essentially free of water; and
   wherein all amounts are percentages by weight based on the total weight of the composition.

2. The composition of claim 1, wherein the amount of water is less than 0.5%.

3. The composition of claim 1, wherein the amount of water is less than 0.1%.

4. The composition of claim 1, wherein the dialkyl sulfosuccinate is diethylhexyl sodium sulfosuccinate.

5. The composition of claim 4, wherein the diethylhexyl sulfosuccinate is present in an amount from about 5% to about 21% by weight of the total weight of the composition.

6. The composition of claim 5, wherein the diethylhexyl sodium sulfosuccinate is present in an amount from about 8% to about 15% by weight of the total weight of the composition.

7. The composition of claim 1, wherein the dialkyl sulfosuccinate is soluble in oil.

8. The composition of claim 1, wherein the *Ricinus Communis* Seed Oil is present in an amount from about 5% to about 50% by weight of the total weight of the composition.

9. The composition of claim 7, wherein the *Ricinus Communis* Seed Oil is present in an amount from about 10% to about 30% by weight of the total weight of the composition.

10. The composition of claim 1, wherein the *Ricinus Communis* Seed Oil stabilizes the diethylhexyl sodium sulfosuccinate.

11. The composition of claim 1, wherein the oil component is selected from olive oil, coconut oil (*Cocos Nucifera* Oil), avocado oil (*Persea Gratissima* oil), apricot oil, sweet almond oil, castor oil, coriander oil, grapeseed oil, rapeseed oil, hazelnut oil, shea butter, palm oil, apricot kernel oil, rice bran oil (*Oryza Sativa* (rice) Bran Oil), corn germ oil (*Zea Mays* Oil, wheatgerm oil, soybean oil, sunflower oil, evening primrose oil, safflower oil, sesame seed oil, passionflower oil, camellia oil, *Vitis Vinifera* (grape) Oil, and mixtures thereof.

12. The composition of claim 1, further comprising a fatty acid mono or dialkanolamide.

13. The composition of claim 12, wherein the fatty acid mono or dialkanolamide is present in amount of about 0.1% to about 10% by weight of the total weight of the composition.

14. The composition of claim 12, wherein the fatty acid mono or dialkanolamide is cocamide mono-isopropanolamide.

15. The composition of claim 1, further comprises propylene glycol.

16. The composition of claim 1, wherein the foaming oil cleanser is sulfate free.

17. An anhydrous foaming oil cleanser comprising:
    (a) from about 8% to about 15% of Diethylhexyl Sodium Sulfosuccinate;
    (b) from about 15% to about 30% of *Ricinus Communis* Seed Oil; and
    (c) from about 35% to about 80% of oils selected from the group consisting of olive oil, coconut oil (*Cocos Nucifera* Oil), avocado oil (*Persea Gratissima* oil), apricot oil, sweet almond oil, castor oil, coriander oil, grapeseed oil, rapeseed oil, hazelnut oil, shea butter, palm oil, apricot kernel oil, rice bran oil (*Oryza Sativa* (rice) Bran Oil), corn germ oil (*Zea Mays* Oil, wheatgerm oil, soybean oil, sunflower oil, evening primrose oil, safflower oil, sesame seed oil, passionflower oil, camellia oil, *Vitis Vinifera* (grape) Oil, and mixtures thereof;
    (d) optional components selected from the group consisting of actives, fragrance, preservatives, and a combination thereof; and
    wherein all amounts are percentages by weight based on the total weight of the composition; and wherein the anhydrous foaming oil cleanser is sulfate-free.

18. The composition of claim 1 further comprising an additive selected from additional surfactants, fragrances, salts, acids, pH adjusters, and mixtures thereof.

19. The composition of claim 18 wherein said actives are selected comprises actives selected from the group consisting of butylated hydroxytoluene, tocopherol, tocopherol derivatives, tocotrienol, tocotrienol derivatives, ascorbic acid derivatives, ascorbyl palmitate, vitamin E, vitamin C, Vitamin A Palmitate and combinations thereof.

20. A method of cleansing skin, comprising applying to skin the composition of claim 1.

21. A foaming oil cleanser comprising:
    (a) from about 8% to about 15% of Diethylhexyl Sodium Sulfosuccinate;
    (b) from about 15% to about 30% of *Ricinus Communis* Seed Oil; and
    (c) from about 35% to about 80% of oils selected from the group consisting of olive oil, coconut oil (*Cocos Nucifera* Oil), avocado oil (*Persea Gratissima* oil), apricot oil, sweet almond oil, castor oil, coriander oil, grapeseed oil, rapeseed oil, hazelnut oil, shea butter, palm oil, apricot kernel oil, rice bran oil (*Oryza Sativa* (rice) Bran Oil), corn germ oil (*Zea Mays* Oil, wheatgerm oil, soybean oil, sunflower oil, evening primrose oil, safflower oil, sesame seed oil, passionflower oil, camellia oil, *Vitis Vinifera* (grape) Oil, and mixtures thereof;
    wherein all amounts are percentages by weight based on the total weight of the composition; and wherein the foaming oil cleanser composition is essentially free of water and free of sulfate.

* * * * *